United States Patent
Rozental et al.

(10) Patent No.: US 9,949,717 B2
(45) Date of Patent: Apr. 24, 2018

(54) ULTRASOUND DETECTOR AND DETECTING DEVICE FOR OPTOACOUSTIC OR THERMOACOUSTIC IMAGING

(75) Inventors: Amir Rozental, Haifa (IL); Daniel Razansky, Munich (DE); Vasilis Ntziachristos, Grafelfing (DE)

(73) Assignee: Helmholtz Zentrum München Deutsches Forschungszentrum für Gesundheitund Umwelt (GmbH), Neuherberg (DE)

( * ) Notice: Subject to any disclaimer, the term of this patent is extended or adjusted under 35 U.S.C. 154(b) by 1240 days.

(21) Appl. No.: 13/982,019

(22) PCT Filed: Feb. 4, 2011

(86) PCT No.: PCT/EP2011/000531
§ 371 (c)(1),
(2), (4) Date: Dec. 13, 2013

(87) PCT Pub. No.: WO2012/103903
PCT Pub. Date: Aug. 9, 2012

(65) Prior Publication Data
US 2014/0114187 A1    Apr. 24, 2014

(51) Int. Cl.
*A61B 8/00* (2006.01)
*G01H 9/00* (2006.01)
*A61B 5/00* (2006.01)

(52) U.S. Cl.
CPC ............ *A61B 8/44* (2013.01); *G01H 9/004* (2013.01); *A61B 5/0095* (2013.01); *A61B 5/0097* (2013.01)

(58) Field of Classification Search
CPC ..... G02F 1/116–1/125; A61B 5/0095–5/0097; G01H 9/004
See application file for complete search history.

(56) References Cited

U.S. PATENT DOCUMENTS 6,839,496 B1    1/2005   Mills et al.
7,206,259 B2    4/2007   Tam et al.
(Continued)

FOREIGN PATENT DOCUMENTS

WO    2010/039950    4/2010

OTHER PUBLICATIONS

Hocker, G. B., "Fiber-Optic Acoustic Sensors with Increased Sensitivity by Use of Composite Structures," *Optics Letters*, Oct. 1979, vol. 4, No. 10, pp. 320-321.
(Continued)

*Primary Examiner* — Serkan Akar
(74) *Attorney, Agent, or Firm* — Stoel Rivers LLP

(57) ABSTRACT

An ultrasound detector adapted for ultrasound detection with medical applications includes an optical waveguide, and at least one Bragg grating, created with a predetermined refractive index modulation amplitude in the optical waveguide, wherein the at least one Bragg grating includes a localized defect in periodicity so that a localized-light resonance portion is formed around the defect, and the localized-light resonance portion has spectral properties capable of being modulated in response to an ultrasound oscillation, wherein the optical waveguide is a non-amplifying optical medium, and the refractive index modulation amplitude is selected such that the localized-light resonance portion is concentrated at the defect in periodicity and the ultrasound oscillation can be sensed by the at least one Bragg grating with an acoustic sensitivity most of which being obtained over the localized-light resonance portion.

34 Claims, 6 Drawing Sheets

(56) References Cited

U.S. PATENT DOCUMENTS

| | | |
|---|---|---|
| 2006/0018595 A1 | 1/2006 | Sasaki |
| 2006/0126435 A1 | 6/2006 | Tam et al. |
| 2007/0123776 A1* | 5/2007 | Aharoni ............ A61B 5/02007 600/437 |
| 2007/0291275 A1 | 12/2007 | Diamond |
| 2008/0043243 A1 | 2/2008 | Lee et al. |
| 2008/0204859 A1* | 8/2008 | Shu ................... G02B 6/02195 359/337.5 |
| 2010/0087732 A1 | 4/2010 | Eberle et al. |

OTHER PUBLICATIONS

Gatti, D. et al,, "Fiber Strain Sensor Based on a π-phase-shifted Bragg Grating and the Pound-Drever-Hall Technique," *Optics Express*, Feb. 4, 2008, vol. 16, No. 3, pp. 1945-1950.

Kersey, A.D. et al., "Fiber Grating Sensors," *Journal of Lightwave Technology*, Aug. 1997, vol. 15, No. 8, pp. 1442-1463.

Agrawal, G.P. et al., "Phase-Shifted Fiber Bragg Gratings and their Application for Wavelength Demultiplexing," *IEEE Photonics Technology Letters*, Aug. 1994, vol. 6, No. 8, pp. 995-997.

Beard, P.C. et al., "Miniature Optical Fiber Ultrasonic Hydrophone Using a Fabry-Perot Polymer Film Interferometer," *Electronics Letters*, Apr. 24, 1997, vol. 33, No. 9, pp. 801-803.

Lamela, H. et al., "Optoacoustic Imaging Using Fiber-Optic Interferometric Sensors," *Optics Letters*, Dec. 1, 2009, vol. 34, No. 23, pp. 3695-3697.

Fisher, N.E. et al., "Ultrasonic Hydrophone Based on Short In-Fiber Bragg Gratings," *Applied Optics*, Dec. 1, 1998, vol. 37, No. 34, pp. 8120-8128.

Shi, C.Z. et al., "Noise Limit in Heterodyne Interferometer Demodulator for FBG-Based Sensors," *Journal of Lightwave Technology*, Oct. 2004, vol. 22, No. 10, pp. 2287-2295.

LeBlanc, M. et al., "Transverse Load Sensing by Use of pi-phase-shifted Fiber Bragg Gratings," *Optics Letters*, Aug. 15, 1999, vol. 24, No. 16, pp. 1091-1093.

Erdogan, T., "Fiber Gratings Spectra," *Journal of Lightwave Technology*, Aug. 1997, vol. 18, No. 16, pp. 1277-1294.

Hoelen, C.G.A. et al., "Three-Dimensional Photoacoustic Imaging of Blood Vessels in Tissue," *Optics Letters*, Apr. 15, 1998, vol. 23, No. 8, pp. 648-650.

Rosenthal, A. et al., "Fast Semi-Analytical Model-Based Acoustic Inversion for Quantitative Optoacoustic Tomography," *IEEE Transactions on Medical Imaging*, Jun. 2010, vol. 29, No. 6, pp. 1275-1285.

Jetzfellner, J. et al., "Performance of Iterative Optoacoustic Tomography with Experimental Data," *Applied Physics Letters*, 2009, vol. 95, cover and pp. 013703-1 to 013703-3.

Rosenthal, A. et al., "Quantitative Optoacoustic Signal Extraction Using Sparse Signal Representation," *IEEE Transactions on Medical Imaging*, Dec. 2009, vol. 28, No. 12, pp. 1997-2006.

Razansky, R. N. et al., "Near-Infrared Fluorescence Catheter System for Two-Dimensional Intravascular Imaging in vivo," *Optics Express*, May 24, 2010, vol. 18, No. 11, pp. 11372-11381.

Buehler, A. et al., "Video Rate Optoacoustic Tomography of Mouse Kidney Perfusion," *Optics Letters*, Jul. 15, 2010, vol. 35, No. 14, pp. 2475-2477.

Ma, R. et al., "Multispectral Optoacoustic Tomography (MSOT) Scanner for Whole-Body Small Animal Imaging." *Optics Express*, Nov. 23, 2009, vol. 17, No. 24, pp. 21414-21426.

\* cited by examiner

ULTRASOUND DETECTOR AND DETECTING DEVICE FOR OPTOACOUSTIC OR THERMOACOUSTIC IMAGING

TECHNICAL FIELD

This disclosure relates to an ultrasound detector comprising an optical waveguide and at least one Bragg grating created in the optical waveguide, wherein the at least one Bragg grating includes a localized defect in periodicity. The disclosure also relates to an ultrasound detecting device including the ultrasound detector and an interrogation device. The disclosure further relates to an imaging apparatus, in particular for opto-acoustic or thermo-acoustic imaging of an object under investigation. The disclosure still further relates to methods of detecting ultrasound oscillations using the ultrasound detecting device.

BACKGROUND

The detection of ultrasound is commonly performed with ultrasound detectors using piezo-electric materials, which convert pressure fields into voltage. Such detectors are characterized by relatively high sensitivity, small size, low cost, flexible design, wide bandwidth, high portability, and the ability to be multiplexed. Currently, piezo-electric detectors are the method of choice for most ultrasound-based bio-medical imaging applications. However, thermoacoustic imaging, and specifically intravascular multispectral optoacoustic imaging may pose stringent requirements on the size and sensitivity of the ultrasound detectors which cannot be met by current piezo-electric detectors. In addition, the vulnerability of piezo-electric detectors to electromagnetic radiation poses difficulties for thermoacoustic-imaging applications.

One application where better acoustic detection is required is intravascular multispectral optoacoustic imaging. Early implementations of such systems relied on the use of an intra-vascular ultrasound (IVUS) detector for measuring the acoustic fields, which is based on piezo-electric technology. However, the miniaturization of the acoustic detector, which allows using IVUS in the coronary arteries, leads to diminished acoustic sensitivity. The exciting optoacoustic pulses should be sufficiently powerful such that the magnitude of the subsequent acoustic signal is higher than the detector's noise floor. However, because of safety restrictions pulses with high energy must be used in low repetition rates on the order of 10 Hz to ensure that the average laser power is below the tissue damage threshold. At such repetition rates, a single volumetric multi-spectral image with a typical length of several centimeters may take many hours to acquire. Such long acquisition times are unacceptable in catheterization procedures because they are invasive. To perform the data acquisition in an acceptable time, the acoustic-detector sensitivity should be improved by orders of magnitude.

Optical detection of acoustic fields has been previously proposed as an alternative to piezo-electric technology. Optical detection schemes are based on the photoelastic effect, where stress or strain in the optical medium leads to changes in its refractive index. The changes in the refractive index are commonly detected using interferometry. Optical detection schemes have been demonstrated for optoacoustic imaging [Beard, P C, and Mills, T N (1997): A miniature optical fiber ultrasonic hydrophone using a Fabry Perot polymer film interferometer, Electronics Letters 33(9), 801-803.]. In contrast to piezo-electric detectors they are not sensitive to external electromagnetic fields and thus are unaffected by the high intensity optical pulses or RF radiation coupled to the imaged object. In addition, since such optical detectors are transparent, they do not block the way of the high-power pulsed beam, allowing for more flexible geometries. However, current optical detectors for ultrasound fail to achieve either the bandwidth or sensitivity of which piezo-electric technology is capable. In addition, multiplexing of sensitive detectors has not been demonstrated. Thus, so far optoacoustic imaging systems which are based on optical detectors for the ultrasound signals did not show significant improvement over more conventional piezo-electric-detector designs in terms of imaging speed and fidelity.

Optical detection schemes proposed for optoacoustic imaging used either 2-beam interferometry (Mach Zehnder or Michelson) [Horacio Lamela et al. "Optoacoustic imaging using fiber-optic interferometric sensors," Optics Letters, Vol. 34, 2009, page 3695-3697] or a Fabry-Perot structure [Beard, P C et al. (1997): A miniature optical fiber ultrasonic hydrophone using a Fabry Perot polymer film interferometer, Electronics Letters 33(9), 801-803]. Fiber Bragg Gratings (FBG's) have been demonstrated for the detection of low frequency ultrasound signals [N. E. Fisher et al. "Ultrasonic hydrophone based on short in-fiber Bragg gratings," Applies Optics, Vol. 34, 1998, pp. 8120-8128]. The limited detection bandwidth, which prevents the use of such schemes in optoacoustic applications, was a result of the relatively large effective size of the detector. In addition, the interrogation was performed using a wideband continuous-wave source. The statistical properties of the light emitted by such sources were analyzed in [C. Z. Shi et al. "Noise Limit in Heterodyne Interferometer Demodulator for FBG-Based Sensors," JOURNAL OF LIGHTWAVE TECHNOLOGY, VOL. 22, NO. 10, OCTOBER 2004, pp. 2287-2295]. Although a quantitative comparison to other sources was not given, it can be shown that interrogation techniques based on a wideband continuous-wave source have an inherently high level of noise which severely limits sensitivity. The reason for this property is that the wide bandwidth of the source is a result of the incoherent nature of the source, i.e., fast random variations in the phase and amplitude of the emitted light. Other wideband-cw-source interrogation techniques can be found in [A. D. Kersey, J. Lightwave Tech. 15, 1142 (1997).]. These techniques are general and can be used to interrogate any linear optical device which exhibits a bandpass spectrum.

If the Bragg grating in an optical fiber includes a π-phase-defect in periodicity, a so-called π-phase-shifted FBG (Pi-phase-shifted FBG) is provided. The π-phase-shifted FBG is characterized by a localized-light resonance portion being formed around the defect and having spectral properties which depend on a mechanical strain exerted on the optical fiber. π-phase-shifted FBG's have been previously demonstrated as load sensors [D. LeBlanc et al. "Transverse load sensing by use of pi-phase-shifted fiber Bragg gratings," OPTICS Letters, Vol. 24, 1999, page 1091], but have not been used for ultrasound detection. The interrogation was performed by inspecting the spectral splitting of the notch in the bandgap spectrum.

U.S. Pat. No. 7,206,259 discloses an ultrasound detector using a fiber sensor with FBG's. The fiber is an active medium, i.e., amplifies the guided light, and with the gratings leads to lasing. The laser light is affected by the acoustic fields. An optical ultrasound receiver is described in US 2010/0087732 A1, wherein a fiber sensor with FBG's is used. The FBG's are used as partially reflecting mirrors to form a Fabry Perot interferometer. The interrogation is performed with narrow-band CW illumination. U.S. Pat. No. 6,839,496 discloses a similar optical fiber probe for photoacoustic material analysis being adapted for forward viewing. Side-viewing optical acoustic sensors and their use in intra-vascular diagnostic probes are described in US 2007/0291275 A1. The optical sensor is a Fabry Perot interferometer. An ultrasound detection system, and material monitoring apparatus and nondestructive inspection apparatus equipped the system is described in US 2008/0043243 A1, wherein a fiber sensor with FBG's is used. The interrogation is done with a wide-band source.

It could therefore be helpful to provide an improved ultrasound detector avoiding disadvantages of conventional detector techniques such as high-sensitivity optical detection of ultrasound fields which is stable against environmental changes such as temperature drifts, pressure variations, and low frequency mechanical vibrations. Furthermore, it could be helpful to provide an improved ultrasound detecting device and an improved imaging apparatus, in particular for optoacoustic or thermoacoustic imaging an object under investigation such as a high-speed multi-spectral optoacoustic or thermoacoustic device implementation adapted for intra-vascular imaging. It could still further be helpful to provide optoacoustic or thermoacoustic imaging device implementations for non-invasive imaging.

SUMMARY

We provide an ultrasound detector adapted for ultrasound detection with medical applications including an optical waveguide, and at least one Bragg grating, created with a predetermined refractive index modulation amplitude in the optical waveguide, wherein the at least one Bragg grating includes a localized defect in periodicity so that a localized-light resonance portion is formed around the defect, and the localized-light resonance portion has spectral properties capable of being modulated in response to an ultrasound oscillation, wherein the optical waveguide is a non-amplifying optical medium, and the refractive index modulation amplitude is selected such that the localized-light resonance portion is concentrated at the defect in periodicity and the ultrasound oscillation can be sensed by the at least one Bragg grating with an acoustic sensitivity most of which being obtained over the localized-light resonance portion.

We also provide an ultrasound detecting device, including the ultrasound detector adapted for ultrasound detection with medical applications including an optical waveguide, and at least one Bragg grating, created with a predetermined refractive index modulation amplitude in the optical waveguide, wherein the at least one Bragg grating includes a localized defect in periodicity so that a localized-light resonance portion is formed around the defect, and the localized-light resonance portion has spectral properties capable of being modulated in response to an ultrasound oscillation, wherein the optical waveguide is a non-amplifying optical medium, and the refractive index modulation amplitude is selected such that the localized-light resonance portion is concentrated at the defect in periodicity and the ultrasound oscillation can be sensed by the at least one Bragg grating with an acoustic sensitivity most of which being obtained over the localized-light resonance portion, and an interrogation device coupled with the at least one ultrasound detector and including an interrogation light source.

We further provide imaging apparatus including an excitation device configured to generate ultrasound in an object by an electromagnetic field input, and the ultrasound detecting device, including the ultrasound detector adapted for ultrasound detection with medical applications including an optical waveguide, and at least one Bragg grating, created with a predetermined refractive index modulation amplitude in the optical waveguide, wherein the at least one Bragg grating includes a localized defect in periodicity so that a localized-light resonance portion is formed around the defect, and the localized-light resonance portion has spectral properties capable of being modulated in response to an ultrasound oscillation, wherein the optical waveguide is a non-amplifying optical medium, and the refractive index modulation amplitude is selected such that the localized-light resonance portion is concentrated at the defect in periodicity and the ultrasound oscillation can be sensed by the at least one Bragg grating with an acoustic sensitivity most of which being obtained over the localized-light resonance portion, and an interrogation device coupled with the at least one ultrasound detector and including an interrogation light source.

We still further provide a method of detecting ultrasound oscillations emanating an object under investigation including creating the ultrasound oscillations in the object under investigation, subjecting at least one ultrasound detector adapted for ultrasound detection with medical applications including an optical waveguide, and at least one Bragg grating, created with a predetermined refractive index modulation amplitude in the optical waveguide, wherein the at least one Bragg grating includes a localized defect in periodicity so that a localized-light resonance portion is formed around the defect, and the localized-light resonance portion has spectral properties capable of being modulated in response to an ultrasound oscillation, wherein the optical waveguide is a non-amplifying optical medium, and the refractive index modulation amplitude is selected such that the localized-light resonance portion is concentrated at the defect in periodicity and the ultrasound oscillation can be sensed by the at least one Bragg grating with an acoustic sensitivity most of which being obtained over the localized-light resonance portion, to the ultrasound oscillations, and interrogating the at least one Bragg grating included in the optical waveguide using the ultrasound detecting device, including the ultrasound detector adapted for ultrasound detection with medical applications including an optical waveguide, and at least one Bragg grating, created with a predetermined refractive index modulation amplitude in the optical waveguide, wherein the at least one Bragg grating includes a localized defect in periodicity so that a localized-light resonance portion is formed around the defect, and the localized-light resonance portion has spectral properties capable of being modulated in response to an ultrasound oscillation, wherein the optical waveguide is a non-amplifying optical medium, and the refractive index modulation amplitude is selected such that the localized-light resonance portion is concentrated at the defect in periodicity and the ultrasound oscillation can be sensed by the at least one Bragg grating with an acoustic sensitivity most of which being obtained over the localized-light resonance portion, and an interrogation device coupled with the at least one ultrasound detector and including an interrogation light source.

BRIEF DESCRIPTION OF THE DRAWINGS

Further details and advantages are described in the following with reference to the attached drawings.

DETAILED DESCRIPTION

Figure 1:
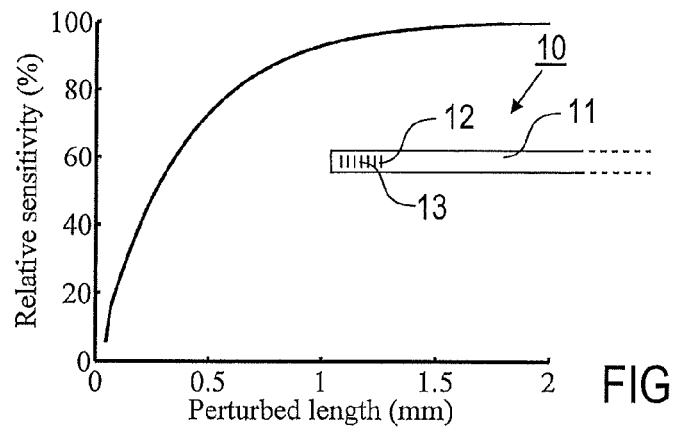
FIG. 1 is a graphical representation of the relative sensitivity of a $\pi$-phase shifted Bragg grating.

We provide an ultrasound detector, in particular adapted for ultrasound detection with medical applications, which may comprise an optical waveguide and at least one Bragg grating, which is created with a predetermined refractive index modulation amplitude in the optical waveguide. Furthermore, the at least one Bragg grating may include a localized defect in periodicity so that a localized-light resonance portion is formed around the defect. The localized-light resonance portion is a geometric region where light traveling in the optical waveguide and interacting with the Bragg grating has a resonance intensity enhancement. The localized-light resonance portion has spectral properties capable of being modulated in response to an ultrasound oscillation (acoustic field), i.e., reflectance or transmission of the at least one the Bragg grating depend on an ultrasound oscillation applied to the Bragg grating. The refractive index modulation amplitude is selected such that the localized-light resonance portion is concentrated at the defect in periodicity. We found that the spatial extension of the light resonance can be reduced by increasing the refractive index modulation amplitude. The refractive index modulation amplitude of the at least one Bragg grating is set during creating of the Bragg grating, e.g., by an irradiation procedure. The refractive index modulation amplitude of the at least one Bragg grating is selected such that the ultrasound oscillation can be sensed by the at least one Bragg grating with an acoustic sensitivity most of which (at least 50%) being obtained over the localized-light resonance portion. In other words, an acoustic modulation of the spectral properties of the Bragg grating is obtained by the effect of the localized-light resonance portion, while eventual contributions from other portions of the grating outside the localized-light resonance portion can be neglected. Thus, the ultrasound oscillation can be sensed by the at least one Bragg grating with spatial resolution so that the ultrasound detector is adapted for imaging applications.

The optical waveguide is a non-amplifying optical medium, preferably a passive waveguide such that lasing cannot occur within the optical waveguide. In other words, the optical waveguide is a passive, non-doped optical waveguide, i.e. the optical waveguide is not adapted for a laser emission. Advantageously, different types of optical waveguides can be used to provide the ultrasound detector. Preferably, the optical waveguide comprises an optical fiber and the at least one Bragg grating comprises a π-phase shifted Fiber Bragg Grating (FBG) created in the optical fiber. As the main advantage, the ultrasound detector can be miniaturized. Further preferably, the optical waveguide comprises a planar waveguide and the at least one Bragg grating comprises a π-phase shifted Waveguide Bragg Grating (WBG). This may have advantages in terms of a higher refractive index modulation leading to stronger light localization in the resonant frequencies and shorter detection length.

Particularly preferably, the optical waveguide of the ultrasound detector has at least one of the following features. First, the refractive index modulation amplitude (Δn) in the core of the waveguide, at the at least one FBG or WBG is at least $1 \times 10^{-4}$, preferably at least $2 \times 10^{-4}$, in particular at least $8 \times 10^{-4}$. Furthermore, the at least one Bragg grating comprises a π-phase shifted FBG which is created with a grating coupling coefficient above $\kappa=0.5$ mm$^{-1}$, in particular above $\kappa=2$ mm$^{-1}$. Contrary to our devices, the grating used by M. LeBlanc et al. (cited above) has a weaker coupling and a low refractive index modulation amplitude resulting in a larger effective detection size, which excludes optoacoustic imaging applications.

The band gap of π-phase-shifted FBG's is equal to $$\Delta \lambda_B = \frac{\kappa \lambda_0^2}{\pi}.$$

In LeBlanc's case, $\Delta \lambda_B \cong 0.2$ nm, corresponding to a coupling parameter $\kappa \cong 0.26$ mm$^{-1}$. This value corresponds to a an effective resonance localization of $\kappa^- \cong 4$ mm and refractive index amplitude modulation of $$\Delta n = \frac{\kappa \lambda_0}{\pi} = 1.28 \times 10^{-4}.$$

According to an example of our technique, taking a higher value for κ ($\kappa=2.58$ mm$^{-1}$) gives an effective resonance localization of $\kappa^{-1}=0.39$=mm, and refractive index amplitude modulation of $$\Delta n = \frac{\kappa \lambda_0}{\pi} = 1.27 \times 10^{-3}.$$

Furthermore, the longitudinal extension of the localized-light resonance portion preferably is below 1.5 mm, in particular below 300 μm. The length of the at least one Bragg grating, in particular FBG or WBG, preferably is below 1 cm, in particular below 5 mm. Furthermore, the spectral width of the grating band gap in transmission preferably is above 0.4 nm, in particular above 1.5 nm.

Further preferably, the optical waveguide of the ultrasound detector is a single mode optical fiber. The detecting element is a π-phase-shifted FBG written in the core of the optical fiber, where only the fundamental mode is guided in the fiber core. The fiber is preferably polarization maintaining to minimize polarization drift of the interrogation light, which would reduce sensitivity.

If the optical waveguide comprises an optical fiber and the at least one π-phase shifted FBG is created at a free end of the optical fiber, advantages for positioning the ultrasound detector in narrow spaces of an object are obtained, e.g., with medical applications. Furthermore, the optical waveguide of the ultrasound detector includes may include one single FBG or WBG only.

Particularly advantageously, the optical waveguide is transparent and insensitive to electromagnetic radiation at least at a position of the at least one π-phase shifted FBG or WBG in the optical waveguide. Thus, positioning the ultrasound detector in the neighborhood of the object under investigation is possible without impairing the excitation of ultrasound in the object by the electromagnetic radiation.

If the optical waveguide comprises an optical fiber, it can be used for both of exciting and detecting the ultrasound. For this purpose, the free end of the optical fiber preferably has a slanted tip laterally reflecting illumination light guided in the optical fiber to a surrounding region of the optical fiber. Preferably, the slanted tip has a slanting angle selected such that the illumination light is reflected to a surrounding region which is located adjacent to a longitudinal position of the localized-light resonance portion of the at least one π-phase shifted FBG. Furthermore, a focusing element focusing illumination light guided in the optical fiber can be provided for concentrating the excitation of ultrasound to a certain region within the object.

Further advantageously, the optical waveguide can include multiple π-phase shifted FBG's or WBG's created in series in the optical waveguide. In this case, advantages for multiplex detection using a single optical waveguide or multiple optical waveguides are obtained. Furthermore, the optical waveguide including the multiple π-phase shifted FBG's or WBG's geometrically can be adapted to the object under investigation. In particular, the optical waveguide can be arranged along a reference surface with a plane or curved extension in space. Thus, a system of multiplexed sensors in particular can be used for whole-body or whole region multi-spectral thermoacoustic imaging, e.g., in animals or human patients.

As a further advantage, the selectivity of the multiplex detection can be improved, if the π-phase shifted FBG's or WBG's are created in the optical waveguide such that the spectral defect resonance of each defect resonance portion is located outside a spectral bandgap of all other π-phase shifted FBG's or WBG's, and/or if the π-phase shifted FBG's or WBG's are created in the optical waveguide with different periods so that the spectral properties of each defect resonance portion are modulated outside a spectral bandgap of all other π-phase shifted FBG's or WBG's.

We also provide an ultrasound detecting device, in particular for photoacoustic or thermoacoustic imaging an object under investigation, which includes the ultrasound detector and an interrogation device coupled with the at least one ultrasound detector and including an interrogation light source, preferably a wideband pulsed interrogation light source. The ultrasound signal is detected by monitoring the shift in the transmission or reflection notch of the at least one Bragg grating using the interrogation light source. The interrogation device generally is adapted for an interferometric detection of the shift in the transmission notch. The interrogation light source is adapted for a wideband interrogation technique. The use of wideband interrogation light sources is an alternative to the narrow-line interrogation schemes which are the standard approach. The difficulty with narrow-line interrogation is that the laser must be tuned to a specific wavelength, which may vary in time. In addition, efficient multiplexing may require using several lasers. Wideband interrogation fits optical devices that exhibit a bandpass spectrum, and can be used to monitor the central wavelength of that spectrum. The source should be wide enough to cover the entire spectral region in which the of the bandpass spectrum may appear. Then the light output of the optical element has the same spectrum as the optical element. The central wavelength of the output is monitored by feeding it to an interferometric setup.

Preferably, the interrogation light source includes a pulsed laser source, in particular creating polarized light pulses having a duration below 1 ns, especially below 50 ps. The main deficiency of the conventional CW technique is that in the wideband sources proposed and demonstrated, the wide bandwidth is a result of a random process. In other words, such sources are inherently noisy. The high noise results in low sensitivity of the detection. On the contrary, our solution uses a pulsed laser to achieve the wide bandwidth. The interrogation is performed using a wideband pulsed laser source, in which the bandwidth is a result of the deterministic amplitude and phase properties of the pulses rather than incoherent light.

Preferably, the optical field contains no power (or minimal, negligible power) outside the temporal support of the pulses. This property can be achieved by additionally applying intensity modulation to the pulses either actively (modulation by external signal), or passively (self-modulation). The pulses are first filtered to limit their bandwidth to be smaller than that of the grating bandgap and are then guided in the optical waveguide to the Bragg grating. For these pulses, the transmission of the grating for each individual pulse is bandpass filtered, and assumes the spectral characteristic of the narrow transmission notch. Variations in the centroid frequency of the notch, caused by the ultrasound field and carried in the transmitted light, can be detected in transmission or reflection by a fast wavelength meter as known in the previous art, e.g., by an unbalanced Mach-Zehnder (MZ) interferometer held at quadrature point by a feedback system. Other types of usable wavelength meters comprise, e.g., a MZ interferometer with modulated optical-path difference, a set of MZ interferometers stabilized to various phases according to an additional external CW source, or a interferometric setup in which the signal is interfered with a narrow-linewidth CW beam or a frequency comb and the beat pattern is recorded with a fast photodiode. The output of the wavelength meter is the absolute wavelength of the signal or rather the relative shifts in wavelength. The reflected signal will have the spectral shape of the filtered laser pulse with the exception of a narrow-bandwidth "hole" created by the low reflectivity of the grating's spectral notch.

The proposed interrogation method combines the benefits of coherent detection with those of wideband excitation. The use of coherent pulsed sources, in which random variations are low, leads to a significantly higher signal-to-noise ratio (SNR) as compared to incoherent sources of the same bandwidth. The use of wideband sources assures that the spectral region of the notch is always illuminated without the need of tuning the source's wavelength to match that of the notch. Thus, the interrogation device can include one single interrogation light source only even with the multiplex detection aspect of the ultrasound detector.

The pulsed laser source can be coupled with an optically dispersive element extending the duration of the light pulses. In this case, advantages in terms of lower maximum power, which allows applying higher amplification to the pulse as performed in the known chirped-pulse-amplification technique.

If the wavelength meter is configured to detect a modulation of spectral properties in the reflection mode, the ultrasound detecting device preferably further comprises a spectral inversion device being configured for interfering detecting light reflected by the at least one π-phase shifted FBG or WBG with a reference beam such that destructive interference is obtained in all wavelengths but those of the spectral properties which are modulated in response to the ultrasound oscillation. In other words, to detect the average frequency of the low-power spectral notch, the "spectral inversion" is employed. Preferably, the spectral inversion device comprises an optical splitter and a Michelson interferometer with two interferometer arms, wherein the optical splitter is arranged for directing the light from the interrogation light source into the interferometer arms, the π-phase shifted FBG or WBG is arranged in one of the interferometer arms, and a reflector is arranged in the other interferometer arm. Thus, spectral inversion is performed by interfering the reflected beam with the reference beam in a way that destructive interference is obtained in all wavelengths but those of the notch. At the notch wavelengths, no interference is nominally obtained, as only the reference beam carries significant energy. As a result, the interference spectrum contains energy only at the transmission-notch wavelengths, i.e., it is an inverted version of the reflection spectrum. The inverted reflection is similar in its properties to the transmission and can thus its centroid wavelength shifts be detected by known methods. The use of spectral inversion enables using wide-band interrogation in the reflection, which allows using the method when only one end of the fiber is accessible, e.g., in intra-vascular applications.

Wideband interrogation techniques have been previously demonstrated for standard gratings (uniform, apodized), which exhibit a bandpass spectrum in reflection. The method has not been demonstrated for π-phase-shifted gratings, which exhibit a bandpass spectrum in transmission. The implementation of the wideband interrogation technique to the transmission of π-phase-shifted gratings is straightforward. However, the detection in reflection mode, required in catheter applications, cannot be achieved using methods known in the previous arts. To solve this problem, the spectral inversion technique is used to turn the bandstop spectrum into a bandpass spectrum.

If the optical fiber includes multiple π-phase shifted FBG's or WBG's created in series in the optical fiber, the ultrasound detecting device may further comprise an optical wavelength demultiplexer device. A Mach-Zehnder modulator can be arranged between the π-phase shifted FBG or WBG and the optical wavelength demultiplexer device or between the interrogation light source and the π-phase shifted FBG or WGB. Detecting light input into or transmitted by the multiple π-phase shifted FBG's or WBG's is intensity modulated using the Mach-Zehnder modulator and light sensitive elements, in particular photodiodes, are arranged at an output of the optical wavelength demultiplexer device, whose output is filtered around a modulation frequency of the Mach-Zehnder modulator.

Alternatively, the transmitted light from the grating cascade is not modulated and fed directly to an optical wavelength demultiplexer. In this case, multiple wavelength meters, in particular multiple Mach-Zehnder interferometers, are arranged at an output of the optical wavelength demultiplexer device for spectrally selective detecting a modulation of spectral properties of the detecting light transmitted by the multiple π-phase shifted FBG's or WBG's in response to an ultrasound oscillation. Variations in the centroid frequency of the notch of each grating can be detected by means known in the previous art, e.g., the unbalanced Mach-Zehnder (MZ) interferometer held at quadrature point by a feedback system.

The advantage of both examples with or without modulation is that they require only one optical source to be used for the entire system. The first example has the additional advantage of requiring less optical equipment, whereas the second example might have advantages in terms of higher sensitivity.

In summary, according to particular features, a method for multiplexing several π-phase-shifted FBG's is described. The gratings are written in a row in the same fiber, where the defect resonance of each grating is located outside the bandgap wavelengths of all other gratings. The detector is interrogated with a coherent pulsed source, whose bandwidth covers the spectral span of all the gratings. For each interrogating pulse, the transmission of the concatenated gratings is hence composed of a set of bands, equivalent to the transmission notches of the gratings. By using an optical wavelength demultiplexer, each spectral band is guided to a different output fiber. Preferably, the transmitted light from the grating cascade is intensity modulated using an unbalanced MZ modulator either before or after the gratings. The optical path difference between the two arms is chosen to be shorter or comparable to the effective coherence length as defined by the spectral width of the gratings' spectral notches. The modulation frequency should exceed the bandwidth of the sensor. After demultiplexing, the output of each output fiber is fed to a fast photodiode, whose signal is filtered around the MZ modulation frequency. The acoustic-signal information is carried in the phase of the filtered signal, and can be extracted by known frequency demodulation.

We further provide an imaging apparatus, in particular for optoacoustic or thermo-acoustic imaging an object under investigation, which includes the ultrasound detecting device above and an excitation device configured to generate ultrasound in the object by an electromagnetic field input, in particular in an optical band or an RF (radio frequency) band. Preferably, the imaging apparatus is configured as an intravascular optoacoustic imaging apparatus.

Preferably, the delivered exciting electromagnetic energy comprises photon energy in the optical spectrum, i.e., the object is illuminated with light. The illumination light comprises at least one characteristic wavelength of at least 1 nm, preferably at least 400 nm, particularly preferred at least 650 nm, and below 5 μm, preferably below 2 μm, particularly preferred below 1.5 μm. For this variant, the excitation device includes a laser source device being adapted for emitting light pulses, preferably in the visible or near-infrared spectra. The light pulses preferably have a duration below 1 μs, particularly preferred below 50 ns. Typically, the illumination light comprises one single illumination wavelength and/or one single light polarization. Accordingly, the energy deposition image can be reconstructed based on the thermoacoustic signals acquired at the single illumination wavelength and/or the single light polarization. Furthermore, the information content of our quantitative imaging advantageously can be increased if the illumination light comprises multiple different excitation wavelengths and/or multiple different light polarizations. With this example, multiple energy deposition images can be separately reconstructed based on the thermoacoustic signals separately acquired at the different illumination wavelengths and/or the different light/field polarizations. As a further option, the energy deposition image can be reconstructed based on a combination of the thermoacoustic signals acquired at the different illumination wavelengths and/or the different light/field polarizations. The combination of the thermoacoustic signals comprises linear or nonlinear signal superpositions, e.g., subtractions, summations, products, ratios or the like.

Alternatively and further preferably, the delivered exciting electromagnetic energy can comprise pulses in the radiofrequency or microwave spectral regions, preferably with pulse durations below 1 µs, most preferably with pulse durations below 50 ns. Accordingly, the excitation device may include a radiation source being adapted for irradiating the imaged object with the radiofrequency pulses.

Preferably, the excitation device includes an illumination waveguide being adapted to illuminate the object under investigation. Using the illumination waveguide has advantages for a targeted excitation of the object in a predetermined region of investigation and/or with a predetermined illumination pattern.

If the imaging apparatus comprises a tube-shaped enclosure accommodating the illumination waveguide and the optical fiber of the ultrasound detector, advantages in terms of compactness of the imaging system, in particular in medical imaging, are obtained. The illumination waveguide and the optical fiber can be positioned such that an offset between the localized defect resonance portion in the at least one π-phase shifted FBG and a tip of the illumination waveguide is smaller than 1 cm, in particular smaller than 5 mm.

Thus, preferably, an intravascular optoacoustic imaging apparatus is described. The ultrasound detecting devices of the apparatus includes two optical fibers: one fiber for guiding exciting optical pulses to the tissue, and the second fiber which contains a π-phase-shifted FBG acting as an acoustic sensor. The grating may be interrogated by our ultrasound detecting device or by known means to perform the acoustic measurement. The illuminating fiber preferably is cleaved with a 45-degree angle to guide light into the wall of the blood vessel. Focusing is applied to the exciting beam by known means. The fibers are positioned such that the offset between the phase shift in the grating and the tip of the illuminating fiber does not exceed a few millimeters. Thus, the FBG-based sensor measures the optoacoustic signal generated by the small portion of the blood vessel which is illuminated. By rotating the illuminating fiber or both fibers, and performing a pullback on both fibers, optoacoustic signals from the entire blood vessels can be acquired. The optoacoustic signals are then processed to obtain the optical absorption map within the blood vessel.

Alternatively, the size of the imaging apparatus even can be further reduced, if the illumination waveguide is included in the optical fiber of the ultrasound detector, in particular in a cladding of the optical fiber. In this case, the apparatus is includes one single optical fiber only. The above offset is provided between the tip of the optical fiber and the position of the localized defect resonance portion in the optical fiber.

With this example, a single-fiber intravascular optoacoustic imaging apparatus is obtained. To this end, a double-cladding fiber may be used, where the exciting pulses are guided in the cladding, whereas the interrogation is performed in the core. The grating may be interrogated by our ultrasound detecting device or by known means to perform the acoustic measurement. The illuminating fiber is cleaved with a 45-degree angle to guide light into the wall of the blood vessel. Focusing is applied to the exciting beam by known means. The grating is written as close as possible to the tip of the fiber. Thus, the FBG-based sensor measures the optoacoustic signal generated by the small portion of the blood vessel which is illuminated. By rotating the fiber, and performing a pullback on it, optoacoustic signals from the entire blood vessels can be acquired. The optoacoustic signals are then processed to obtain the optical absorption map within the blood vessel.

To implement the above rotation and translation of the single or double fiber examples, the imaging device preferably comprises a rotation drive adapted for rotating the illumination wave guide relative to the object under investigation, and/or a translation drive adapted for translating the illumination wave guide and the optical fiber relative to the object under investigation.

The thermoacoustic signals can be subjected to preprocessing before the image reconstruction. Advantageously, preprocessing by an analog or digital signal processing operation, e.g., filtering, integration, differentiation, may improve the result of the image reconstruction.

We still further provide methods of detecting ultrasound oscillations emanating an object under investigation, which generally comprise the step of detecting the ultrasound oscillations using the ultrasound detecting device. Preferred examples of the methods are characterized by operating the above examples of the ultrasound detecting device.

Preferably, ultrasound oscillations are created with an excitation device which is configured to generate ultrasound in the object by an electromagnetic field input in an optical band or an RF band, wherein the excitation device is arranged with a distance from the object. Preferably, the medium between the object and detector is acoustically matched to the imaged object. Alternatively, the at least one ultrasound detector can be arranged on a surface of the object under investigation, i.e., in contact with the object surface.

Applications are available, e.g., in medical imaging or material investigations. According to a particularly preferred application, the ultrasound detector is arranged in a vascular portion of a biological organism. For imaging tissue around the vascular portion, the ultrasound detector is moved, in particular rotated and/or translated, in the vascular portion. In particular, the methods can be used to construct an intravascular catheter for multi-spectral thermoacoustic imaging to characterize the progress of various vascular diseases, namely atherosclerosis. In particular, the methods can be used for accurate extraction of biomarker concentration, e.g., characterization of vascular trees, tumor angiogenesis, blood oxygenation, or in molecular imaging studies with various targeted contrast agents, including dyes, light-absorbing nano-particles and fluorochromes.

Accordingly, a non-invasive optoacoustic or thermoacoustic imaging system is described. The excitation is performed by delivering electromagnetic energy into the imaged specimen. The detection is performed by the multiple-element fiber sensor. The different detecting elements along the fibers are positioned around the imaged specimen or on one of its sides to provide a tomographic or semi-tomographic view. Additionally, the fiber may be rotated, translated, or pulled to provide additional measurement points. Because the detector is small, transparent, and unaffected by electromagnetic radiation it may be positioned between the exciting electromagnetic source and the specimen. The optoacoustic or thermoacoustic signals are then processed to obtain an absorption map within the object.

EXAMPLES

Preferred aspects are described in the following with exemplary reference to optoacoustic or thermoacoustic tomography. This disclosure is not restricted to these examples, but can be equally applied to other methods utilizing opto- or thermoacoustic interactions, for instance Photo-Acoustic Tomography (PAT), multispectral optoacoustic tomography (MSOT), thermoacoustic tomography (TAT) or Near-Field Radiofrequency Tomography (NRT). In addition, our methods and devices can be applied to other acoustic imaging schemes such as sonography. This disclosure is described with reference to features of the ultrasound detector, the ultrasound detecting device and the imaging apparatus. Exemplary reference is made to configurations wherein the optical waveguide comprises an optical fiber and the at least one Bragg grating comprises a π-phase shifted Fiber Bragg grating (FBG). Our methods and devices can be implemented in an analogue way using an optical waveguide, which comprises a planar waveguide, wherein the at least one Bragg grating comprises a π-phase shifted Waveguide Bragg grating (WBG). Details of exciting acoustic fields in the object and constructing an image of the object based on the detected ultrasound signals are not described as they can be implemented as with conventional optoacoustic or thermoacoustic imaging methods.

Ultrasound Detector (Acoustic Detector) Including a π-Phase-Shifted FBG

The insert of FIG. 1 schematically illustrates a first example of an ultrasound detector 10, which comprises an optical fiber 11 including a π-phase shifted FBG 12 with a localized defect 13 in periodicity. The π-phase-shifted FBG 12 is characterized by a bandpass spectrum in its reflection with a narrow notch nominally in the middle of the spectrum. The high reflection, whose nominal value is 100%, is a result of the bandgap effect, whereas the notch, whose nominal reflection is 0, is a result of the π-phase shift, nominally created in the middle of the grating, which is a defect in the otherwise periodic structure. The nominal reflection wavelength of the grating is given by Bragg's law:

$$\lambda_N = 2n_{eff}\Lambda \quad (1)$$

where $n_{eff}$ is the effective refractive index in the fiber and $\Lambda$ is the grating period. When uniform pressure is applied to the fiber, it causes a change in the refractive index of the fiber and grating period. The combined effect of the two phenomena may create a shift in the spectrum given by the following equation:

$$d\lambda_N = 2n_{eff} d\Lambda + 2\Lambda \, dn_{eff} \quad (2)$$

where $dn_{eff}$ and $d\Lambda$ are the variations in $n_{eff}$ and $\Lambda$, respectively.

When pressure is applied to only a section of the grating, a simple shift is no longer obtained, but rather a more complicated spectral distortion. Nonetheless, Eq. 2 is still valid to the shift in the spectrum notch as long as the pressure is applied around the phase shift. The reason for this effect is that light at the notch wavelengths is highly concentrated around the location of the π-phase shift, and as a result it is mostly affected optical variations in that region. An additional implication of this is that the notch spectrum is not sensitive to pressure applied outside the neighborhood of phase shift. The 1/e width of the field distribution around the phase shift for the notch wavelengths is approximately given by $2\kappa^{-1}$, which is the coupling coefficient of the grating. Thus, an optical detecting scheme based on monitoring shifts in the spectrum notch will have increased sensitivity over a length of $2\kappa^{-1}$.

The effect of localized sensitivity is demonstrated henceforth in a numerical simulation. The π-phase-shifted FBG has a coupling coefficient of $\kappa = 2.58$ mm$^{-1}$ and a length of L=2.38 mm. The spectral shift of the grating spectrum is calculated under local perturbation using the transfer-matrix method [T. Erdogan, "Fiber Grating Spectra," JOURNAL OF LIGHTWAVE TECHNOLOGY, VOL. 15, 1997, pp. 1277-1294]. The perturbation is obtained by slightly increasing the refractive index of the grating over the region of interest, though perturbation in the grating period is mathematically equivalent. The perturbation is applied symmetrically around phase shift, and the respective resonance shift is divided by the shift obtained when the perturbation is applied to the entire grating length. FIG. 1 shows the relative shift in the resonance as a function of the perturbed length. According to FIG. 1, a localized-light resonance portion of 270 μm around the phase shift is responsible for 50% of the grating's acoustic sensitivity. This value corresponds to the scale of the field distribution around the π-phase shift, which has an effective length of $\kappa^{-1} = 388$ μm. The refractive index modulation amplitude ($\Delta n$) of the grating 11 is about $1.3 \times 10^{-3}$.

Ultrasound Detecting Device and Interrogation Method

Figure 2:
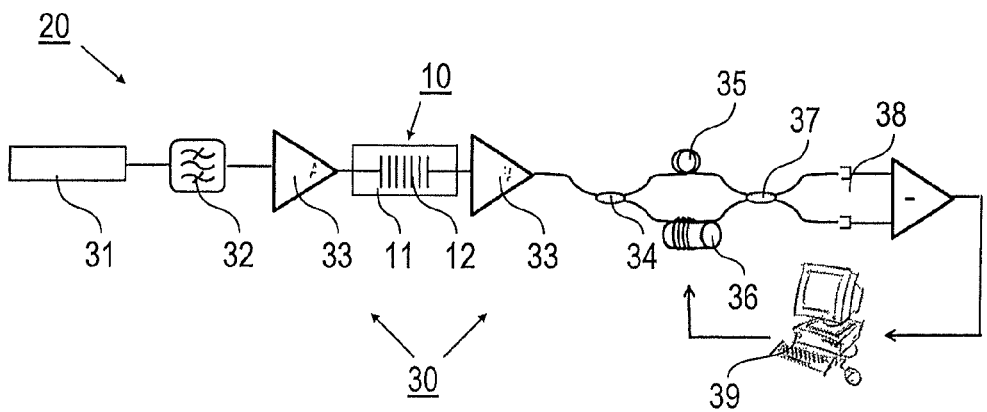
FIG. 2 is an illustration of an ultrasound detecting device adapted for an interrogation of the Bragg grating in a transmission mode.

Examples of an ultrasound detecting device 20 including the ultrasound detector 10 and an interrogation device 30, 40 and our interrogation method are described in the following with reference to FIGS. 2 to 4. With these examples, the interrogation device 30 comprises an interrogation light source 31 (pulsed laser source 31), an optical filter 32, a pulse amplifier 33 (e.g., an erbium doped fiber amplifier) arranged before the ultrasound detector 10, another pulse amplifier 33 arranged after the ultrasound detector 10 and a Mach-Zehnder interferometer (MZ interferometer) 34-39. According to FIG. 3, the interrogation device additionally includes a spectral inversion device 40. The example of FIG. 4 is designed as the example of FIG. 2 with the only difference that the optical fiber 11 of the ultrasound detector 10 in FIG. 2 is replaced by a planar waveguide 14 including a π-phase shifted WBG 15. Within the ultrasound detecting devices 20, the interrogation light travels from the interrogation light source 31 via the ultrasound detector 10 to the MZ interferometer through optical fibers. Polarization maintaining fibers are used to maintain a single polarization.

Figure 5:
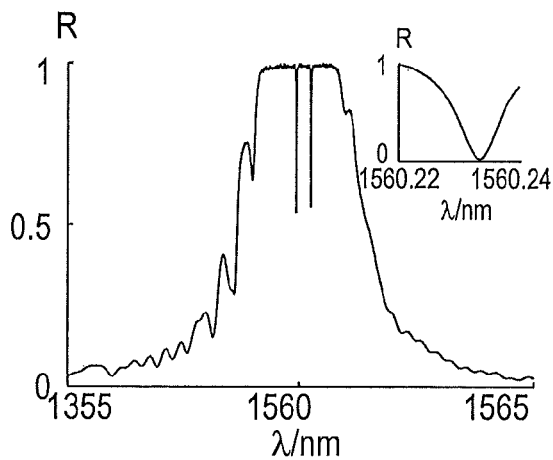
FIG. 5 is a reflection spectrum of a π-phase shifted Bragg grating created in an optical fiber.

The interrogation light source 31 is, e.g., a 90-fs laser with a repetition rate of 100 MHz, output power of 60 mW and spectral width of over 40 nm (Menlo Systems GmbH, Martinsried, Germany). The optical filter 32 has a FWHM spectral width of 0.3 nm and is tuned to the frequency of the ultrasound detector 10 resonance. In the illustrated examples, the detection bandwidth is set to, e.g., 20 MHz. The FBG 12, whose spectrum is shown in FIG. 5, has a bandgap span of 1.38 nm and a FWHM resonance width of 8 pm, corresponding to $\kappa = 2.58$ mm$^{-1}$ and L=2.38 mm. These values correspond to spectral-inversion efficiency of 0.66, i.e., the defect-mode resonance constitutes 66% of the power of the inverted spectrum.

After the reflection of the interrogation light pulses with the ultrasound detector 10 and an amplification of the light pulses with the second pulse amplifier 33, the amplified light pulses are split with a 50/50-coupler 34 into the arms of the MZ interferometer. The first arm of the MZ interferometer is an optical path delay (OPD) 35 of approximately 8 cm. The second arm of the MZ interferometer includes a piezoelectric modulator 36. The portions of the light pulses travelling through the first and second arms are superimposed at the second 50/50-coupler 37 and photo-electrically sensed with a photosensor 38. The output signal of the photosensor 38 is amplified and input to a control device 39 (implemented with a computer), which generates a control signal for setting the modulator 36. The MZ interferometer is stabilized to its quadrature point. With the photosensor 38, the control device 39 and the modulator 36, a control loop is implemented, which is used for sensing acoustically induced wavelength or frequency variations of the light resonance of the FBG 12.

Figure 3:
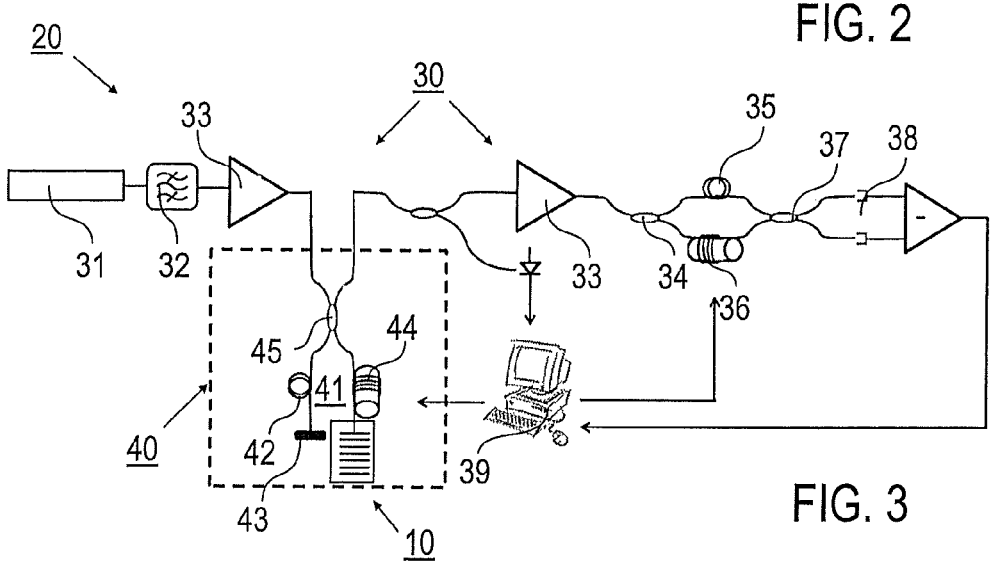
FIG. 3 is an illustration of an ultrasound detecting device adapted for an interrogation of the Bragg grating in a reflection mode.
Figure 4:
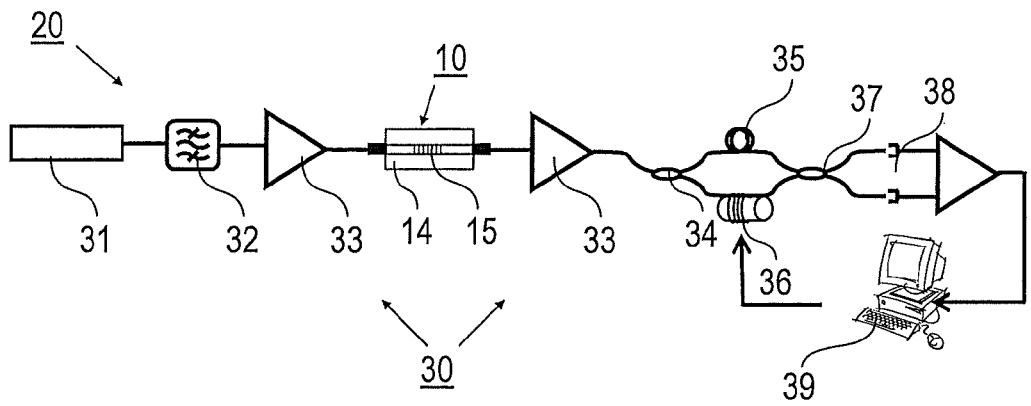
FIG. 4 is an illustration of an ultrasound detecting device wherein the Bragg grating is arranged in a planar waveguide.

According to FIG. 3, the control device 39 is additionally used to control the spectral inversion device 40. The spectral inversion device 40 includes a Michelson interferometer 41. In a first arm, an optical path delay 42 and a reflector 43, like, e.g., a mirror are arranged. In the second arm of the Michelson interferometer 41, a modulator 44 and the ultrasound detector 10 are arranged. The modulator 44 includes a piezo-electric fiber stretcher. The spectral inversion is implemented using the Michelson interferometer 41 stabilized to destructive interference on its output arm. A feedback signal, generated with the control device 39 and fed into the modulator 44 (piezo-electric fiber stretcher on one of the interferometer arms (Optiphase, Inc., Van Nuys, Calif., USA) with a response bandwidth of 100 kHz) is used to stabilize both interferometers.

Figure 6:
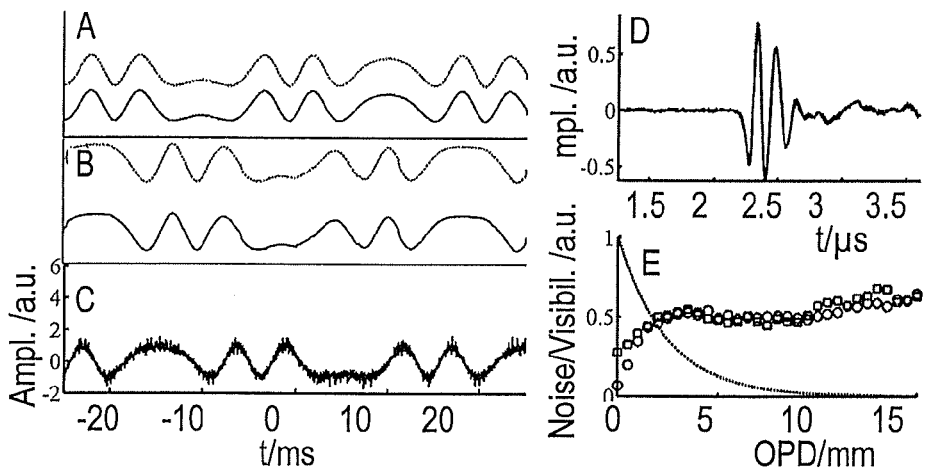
FIG. 6 shows experimental results obtained with the ultrasound detecting device according to FIG. 2 or 3.

FIGS. 5 and 6 illustrate experimental results obtained with the examples of FIGS. 2 and 3. FIG. 5 shows the reflection spectrum of the grating 12, as obtained using unpolarized light. The two dips in the bandgap correspond to the two polarization modes. The inset shows in high resolution the resonance of the slow-axis polarization obtained with a polarized source.

In a first experiment, the performance of the spectral-inversion scheme was tested. For this, the MZ interferometer 34-37 was not stabilized, but rather fed with a 25 Hz sinusoidal signal. FIGS. 6A and 6B show the differential signal at the output of the interferometer for transmission and reflection, respectively (solid curves). The signals are also shown with the offset obtained when the measurement was performed for a single interferometer arm (dashed curves). For the transmission, the obtained visibility was 0.42, corresponding to an OPD of 8.2 cm. In the reflection, the visibility decreased to 0.27, corresponding to spectral-inversion efficiency of approximately 0.64. The spectral-inversion efficiency can be increased by improving the balance of the Michelson interferometer 41 and by using a narrower and steeper optical bandpass filter 32. The high visibility obtained in the reflection measurement provides experimental proof of the spectral inversion. For comparison, when the mirror in the Michelson interferometer was removed, no visible interference was obtained in the reflection.

FIG. 6C shows transmission measurement with the source replaced by an amplified spontaneous emission source. Comparing the optical noise obtained with both measurements showed an 18-fold decrease in the standard-deviation of noise over the measurement bandwidth when the pulsed laser is used.

In a second experiment, the scheme was applied for broadband measurement of ultrasound fields. For this, a flat round ultrasonic transducer with a diameter of 6 mm (Model V323-SM, Olympus-NDT, Waltham, Mass.) was fed with 66 ns square electric pulse. The generated field was first measured by a pre-calibrated hydrophone (Model HPM1/1, Precision Acoustics Ltd., Dorset, U.K.) and was found to have a peak amplitude of approximately 175 kPa at a distance of 3.3 mm from the transducer's surface. The grating was then positioned in parallel to the transducer's axis at a similar distance. Because of the slow response of the feedback scheme, the fast resonance variations induced by the acoustic fields were not compensated for by the MZ interferometer stabilization, but were rather recorded by the differential signal at the output of the interferometer. FIG. 6D shows the measured acoustic fields for the reflection (solid curve) and transmission (dashed curve), attaining no significant difference between the two measurements.

The last measurement aimed at analyzing the noise sources in our ultrasound detecting devices. The laser pulses propagates through the 0.3 nm optical bandpass filters 32 into the MZ interferometer. The interferometer is stabilized to quadrature point while the noise and visibility are measured for different OPD's with 0.5 mm increments. The noise measurement is performed by calculating the standard deviation of the output voltage obtained over duration of 10 µs with 20 MHz bandwidth. The noise data (square markers) and visibility (solid curve) are shown in FIG. 6E. While the visibility is the same for CW and pulse interrogation, its underpinnings are different. In CW interferometry, visibility is determined by the phase correlation between the two beams, whereas in pulse interferometry, it is determined by pulse overlap, where zero visibility indicates no overlap. Thus, for a pulsed source with no power outside the support of the pulses, no interference noise should be obtained when the visibility vanishes. Nonetheless, FIG. 6E shows no decrease in noise as the visibility vanishes. The measurement was repeated with an optical spontaneous emission CW source instead of the pulsed laser and reached similar results for the noise data (round markers). These measurements indicate that in the pulse-interferometry setup, there is indeed a contribution to the noise from temporal regions outside the support of the pulses. Thus, modulation of the pulse-train to eliminate parasitic fields outside the pulse support can significantly increase the SNR of the system.

Sensor Multiplexing

Figure 7:
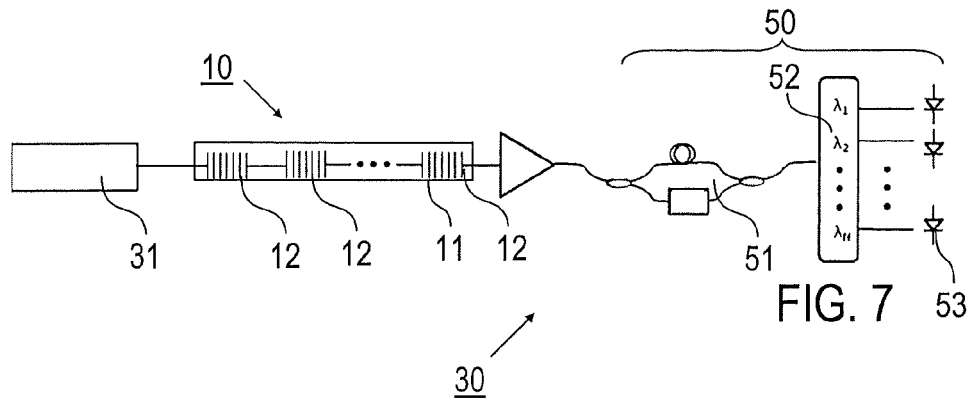
FIGS. 7 to 9 show three implementations for multiplexing the π-phase shifted FBG sensor scheme described in FIG. 2 or 3.
Figure 8:
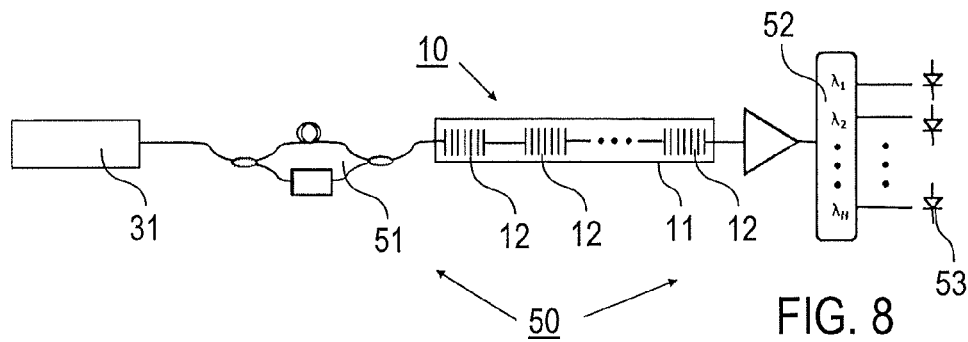
Figure 9:
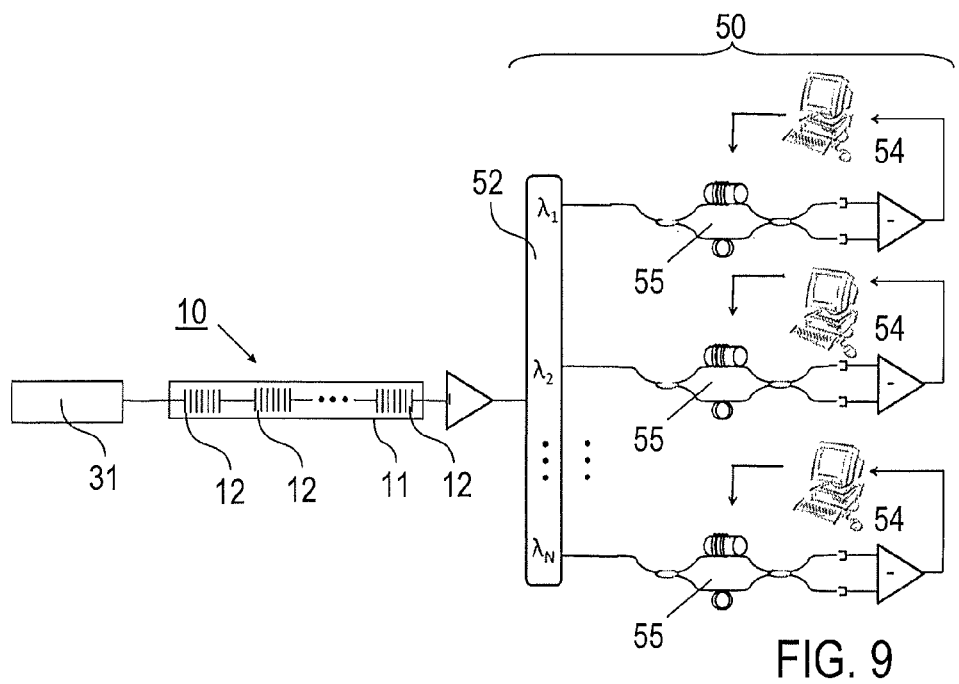

If acoustic fields are to be detected at different locations in the object simultaneously, multiple FBG's or WBG's are provided in the optical fiber or planar waveguide, respectively. Each of the Bragg gratings has a different periodicity being adapted to a different interrogation light wavelength. As an example, up to 100 or even more Bragg gratings (FBG's 11 or WBG's 15) can be arranged in the optical waveguide of ultrasound detector 10. FIGS. 7 to 9 illustrate examples of ultrasound detecting device 20 being provided with an optical wavelength demultiplexer device 50. The operation of the various types of demultiplexer devices 50 are described in the following.

Our multiplexing/demultiplexing method is wavelength based and utilizes the wide bandwidth of the interrogating source 31 and wavelength encoded nature of FBG's 12 or WBG's 15. The single Bragg grating in the one-element sensor (see insert in FIG. 1) is replaced by N FBG's written in series. The gratings are written with different periods so that the transmission notch of each grating is outside the bandgap wavelengths of all other gratings. Thus, the combined grating structure exhibits N narrow-band transmission notches. FIGS. 7 to 9 show three interrogation methods to simultaneously monitor the central wavelength of the transmission notches of all N gratings. In all methods the gratings are interrogated in transmission using the optical wavelength demultiplexer device 50.

In the first two methods, a modulated unbalanced MZ modulator 51 is placed either after (FIG. 7) or before (FIG. 8) the gratings 12. The optical path difference between the two arms is chosen to be shorter or comparable to the effective coherence length as defined by the spectral width of the gratings' spectral notches. The modulation performed in the MZ modulator 51 encodes the wavelength-shift of the gratings 12 in the intensity of transmitted beam. The modulation frequency is selected to be essentially higher than the bandwidth of the ultrasound detector 10, yet smaller than the detection bandwidth of the photodiodes and electronic components used to detect the modulated signal 53.

After passing through the optical demultiplexer 52 of the optical wavelength demultiplexer device 50, the transmitted intensity-modulated beam on each branch hold the information on the wavelength-shift of the respective grating in its modulation frequency. The optical signal on each branch is fed to a wideband photodiode 53 which transforms it to an electrical signal. The electrical signal is then filtered around the modulation frequency. The phase information of the signal is extracted by known frequency demodulation.

In the third method (FIG. 9), a plurality of MZ interferometers 55 are positioned after the optical demultiplexer 52 of the optical wavelength demultiplexer device 50. As a result, this method requires using N MZ interferometers. The conversion of the wavelength-encoded information in FBG's 11 into intensity encoded information is done similarly to the implementation for a single FBG. Specifically, the MZ interferometers 55 are held at quadrature point using a feedback loop 54. The feedback bandwidth is smaller than that of the ultrasound detector 10, and thus does not compensate for variations in the FBG's' wavelengths created by the ultrasound signals. Instead, only low frequency disturbances to the ultrasound detector 10 such as temperature drift and mechanical vibrations, are compensated for, whereas acoustic field in the ultrasound regime lead to wavelength change in the FBG's 12 that takes the MZ interferometers 55 out of quadrature. Thus, only the high-frequency acoustic fields are recorded in the intensity of the output of the interferometer.

Optoacoustic Catheter Apparatus

With a preferred application, the imaging apparatus 60 is an opto-acoustic catheter apparatus, in particular for medical imaging of tissue, e.g., of a human patient. Preferred examples of the opto-acoustic catheter apparatus are schematically illustrated in FIGS. 10 to 14. The opto-acoustic catheter apparatus 60 is particularly adapted for imaging biological tissue including a wall 1 of a blood vessel 2 and optionally the surrounding tissue 3 (see FIGS. 11, 13).

Figure 10:
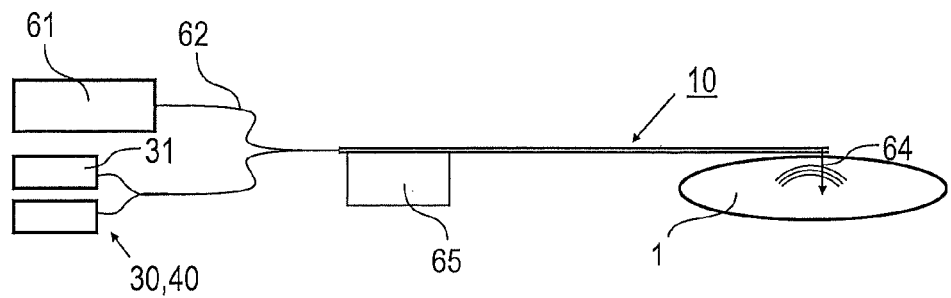
FIG. 10 is a schematic illustration of an imaging apparatus adapted for vascular imaging.

FIG. 10 schematically shows the opto-acoustic catheter apparatus 60 comprising an excitation device 61, the ultrasound detector 10 and the interrogation device 30, 40. The excitation device 61 comprises, e.g., a pulsed laser source controlled to emit a predetermined excitation light in a wavelength range of, e.g., 650 nm to 900 nm, or 1100 nm to 1300 nm and an illumination waveguide 62 adapted to guide the excitation light into the object 1 under investigation (see arrow 64). Ultrasound excited in the object in response to the illumination is sensed with the ultrasound detector 10 and the interrogation device 30, 40. The ultrasound detector 10 provides a catheter part of the opto-acoustic catheter apparatus 60. It can be introduced into a hollow space, in particular a vessel, as it is known from conventional catheters. The ultrasound detector 10 is connected with a drive mechanism 65 (pull-back and/or rotation mechanism), which is adapted to adjust the position and/or orientation of the ultrasound detector 10 relative to the object 1, in particular in a blood vessel 2. Additionally, a processor unit (e.g., a computer, not shown) is provided for reconstructing images based on the detected ultrasound signals (see FIGS. 15, 16).

Figure 12:
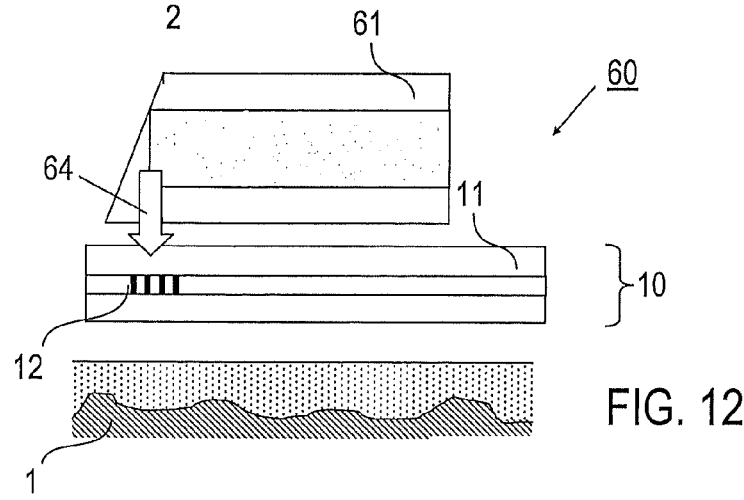
Figure 13:
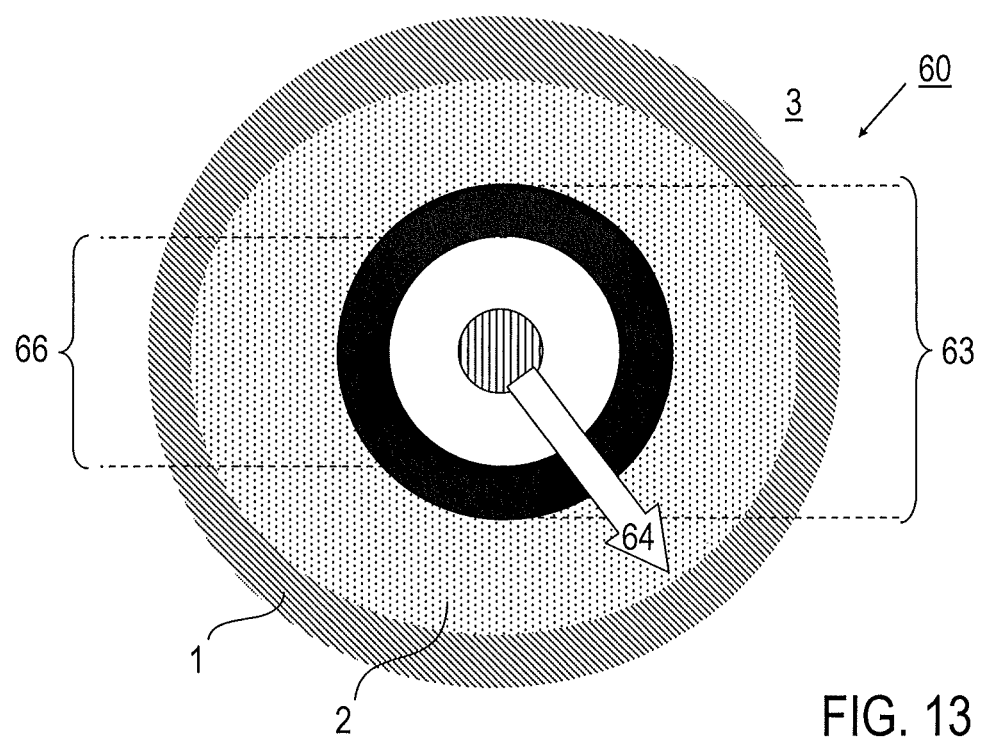
FIGS. 13 and 14 show cross-sectional and side-view illustrations of a single-fiber catheter apparatus.
Figure 14:
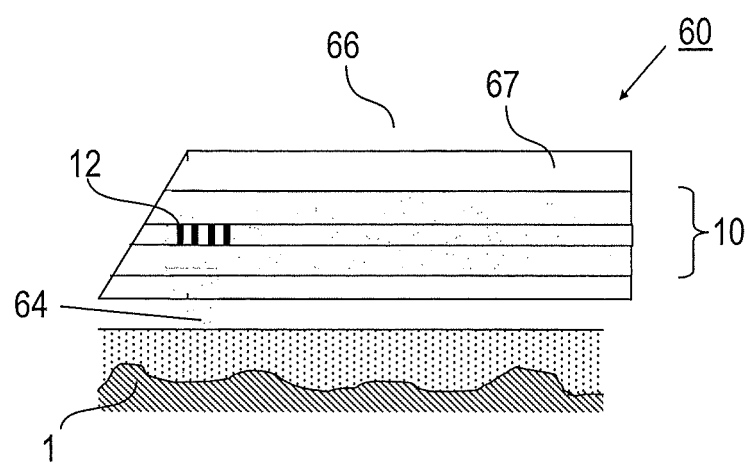

With vascular imaging applications, our imaging apparatus, in particular the catheter part thereof fulfills two functions: delivering the pulsed exciting light into the blood-vessel wall and measuring the subsequent acoustic field. These two functions can be performed using either two separate fibers (FIGS. 11, 12) or a single fiber (FIGS. 13, 14). The illustrations of FIGS. 11 to 14 refer to the two-fiber or the single-fiber design to provide the optical waveguide of the ultrasound detector and the illumination waveguide of the excitation device of the imaging apparatus. Further details of the opto-acoustic catheter apparatus, like the interrogation device and further details of the excitation device are not illustrated in FIGS. 11 to 14. The interrogation device can be implemented, e.g., according to one of the examples of FIGS. 2, 3 and 7 to 9.

The acoustic signals measured by system are included image information on an optoacoustic image or multi-spectral optoacoustic images. The processing of reconstructing the image(s) can be performed using a simple delay and sum approach (C. G. A. Hoelen et al., "Three-dimensional photoacoustic imaging of blood vessels in tissue," OPTICS LETTERS, Vol. 23, 1998, pp. 648-650), or using model-based reconstructions (A. Rosenthal et al., "Fast semi-analytical model-based acoustic inversion for quantitative optoacoustic tomography," IEEE Trans. Med. Imaging, Vol. 29, pp. 1275-1285, 2010). The effect of blood attenuation can be corrected for by using light propagation models (Jetzfellner, T et al. "Performance of iterative optoacoustic tomography with experimental data," APPLIED PHYSICS LETTERS 95(1); 013703 (2009)) and/or by exploiting the spatial properties of optoacoustic images (A. Rosenthal et al. "Quantitative optoacoustic tomography using sparse signal representation," IEEE Transactions on Medical Imaging, 28(12), pp. 1997-2006, 2009.).

Two-Fiber Design

Figure 11:
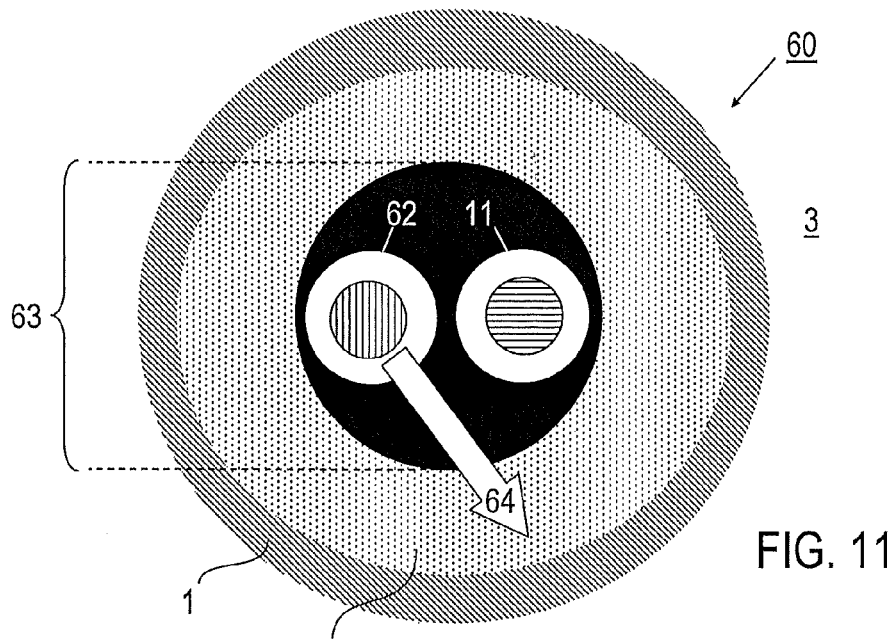
FIGS. 11 and 12 are schematic cross-sectional and side-view illustrations of a two-fiber catheter apparatus.

In the two fiber design, the illumination is performed using one fiber representing the illumination waveguide 62 being adapted to illuminate the object under investigation, whereas the acoustic detection is performed by the other representing the optical fiber 11 of our ultrasound detector. The illumination waveguide 62 may be single mode or multi mode fiber, whereas the detecting optical fiber 11 should be single mode, and preferably polarization maintaining. The two-fiber catheter 60 is schematically shown in FIGS. 11 and 12. FIG. 11 shows a cross section of the catheter geometry within the blood vessel 2. The three concentric circles in the FIG. 10 represent a tube-shaped enclosure (sheath) 63 guiding both fibers into the blood vessel 2, the lumen of the blood vessel 2 (dotted pattern), and the wall 1 of the blood vessel (diagonal pattern). The tube-shaped enclosure 63 contains two chambers, where each chamber is used for a different fiber. Light 64 emanating from the illumination waveguide 62 to the blood-vessel wall 1 is shown with an arrow. FIG. 12 shows a side view of the catheter 60. Because the FBG-based ultrasound detector 10 is transparent, the two fibers 11, 62 can be positioned such that the exciting light beam 64 passes through the grating 12 in fiber 11 for some of the orientations of the illumination waveguide 62.

The tip of the illumination waveguide 62 is slanted relative to a longitudinal axis of the illumination waveguide 62 for reflecting the excitation light in a radial direction. Furthermore, the tip of the illumination waveguide 62 may contain a focusing element to partially focus the beam to the wall 1 of the blood vessel 2. Focusing can be performed by known methods such as Gradient-index lenses or curved fiber tip. Partial focusing is preferred over strong focusing or no focusing as it leads to minimum variations in the maximum intensity the beam 64 in the case of non-scattering non-absorbing medium. Although the blood-vessel 2 and its blood-filled lumen are optically scattering and absorbing, the short propagation length of few millimeters allows for the focusing properties to be partially preserved.

For each position and orientation of the catheter 60, the measured optoacoustic signal corresponds to the illuminated section of the blood vessel 2. To image the entire blood vessel 2, the catheter 60 should be rotated and translated within the blood vessel 2. The rotation may be applied solely to the illumination waveguide 61. In this case, the angular resolution is determined by the angular width of the exciting light beam 64. To improve the angular resolution, the optical fiber 11 of the ultrasound detector 10 may be pre-processed to induce angular-dependent detection sensitivity. Specifically, the fiber may be coated with an acoustically dampening material for most of its circumference, excluding only a small-angle window. In such a structure, the sensitivity will be higher for targets in front of the small-angle window than for those which have an offset with respect to the window. In this case, both fibers 11, 61 should be simultaneously rotated to improve resolution. Translation is performed on both fibers 11, 61, or on the entire catheter structure using the drive mechanism 65. The rotation and translation are performed using methods known in the previous art, e.g., the method described by D. Razansky et al. "Near-infrared fluorescence catheter system for two-dimensional intravascular imaging in vivo," OPTICS EXPRESS; 18(11); 11372-11381 (2010)).

Single-Fiber Design

In the single-fiber design, the illumination and acoustic detection are performed using the same fiber. The fiber may be either single mode, or double cladding. In the former case, both the exciting beam and interrogating beam are guided in the core of the fiber. In the latter case, the exciting light beam is guided in the inner-cladding 67 of the fiber, whereas the interrogating beam is guided in the core. The inner-cladding of the fiber provides the illumination waveguide. FIG. 13 shows a cross section of the catheter geometry within the blood vessel 2. The three concentric circles in the figures represent the tube-shaped enclosure (sheath) 63 guiding the fiber 66 into the blood vessel 2, the lumen of the blood vessel 2 (dotted pattern), and the wall 1 of the blood vessel 2 (diagonal pattern). The tube-shaped enclosure 63 contains a single chamber in which the fiber 66 is guided. Light 64 emanating from the fiber 66 to the blood-vessel wall 1 is shown with an arrow. FIG. 14 shows a side view of the catheter 60.

Again, the tip of the fiber may contain a focusing element to partially focus the beam to the wall of the blood vessel. Focusing can be performed by method known in the previous art, such as Gradient-index lenses or curved fiber tip. Partial focusing is preferred over strong focusing or no focusing as it leads to minimum variations in the maximum intensity the beam in the case of non-scattering non-absorbing medium. Although the blood-vessel and its blood-filled lumen are optically scattering and absorbing, the short propagation length of few millimeters allows for the focusing properties to be partially preserved.

The FBG 12 should be written as close as possible to the tip of the fiber 64 to reduce the distance and angle from the position of the ultrasound detector 10 to the illuminated part of the blood vessel 2. Because the grating's detecting portion is located in its center, it will be offset from the illumination by at least half the grating's length. The effect of this offset on the acoustic-signal acquiring can be reduced by guiding the exciting beam 64 into the blood vessel not exactly perpendicular to the fiber, but rather with a small incline. This could reduce the offset between the sensor and the illuminated part of the blood vessel 2.

For each position and orientation of the catheter 60, the measured optoacoustic signal corresponds to the illuminated section of the blood vessel 2. To image the entire blood vessel 2, the fiber 66 should be rotated and translated within the blood vessel 2. To improve the angular resolution, the fiber 66 may be pre-processed to induce angular-dependent detection sensitivity. Translation is performed on the fiber 66, or on the entire catheter structure using a pull-back mechanism of the drive mechanism 65 (see FIG. 10). The rotation and translation are performed using known methods (cited above).

Noninvasive Thermoacoustic Imaging Apparatus

Figure 15:
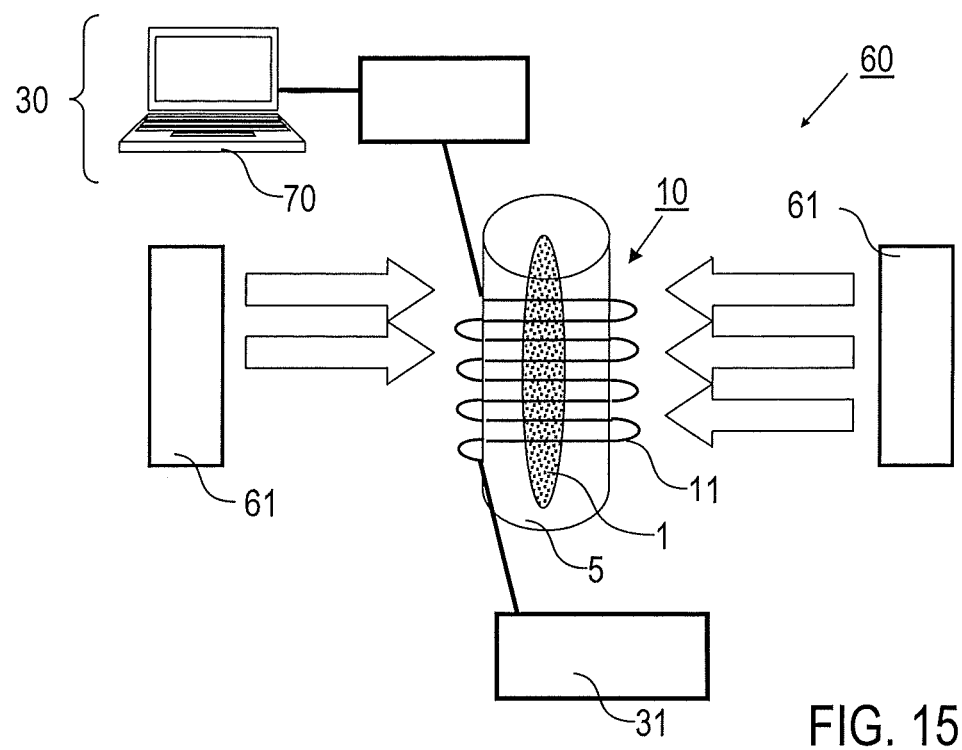
FIGS. 15 and 16 are schematic illustrations of an imaging apparatus adapted for non-invasive imaging of an object.
Figure 16:
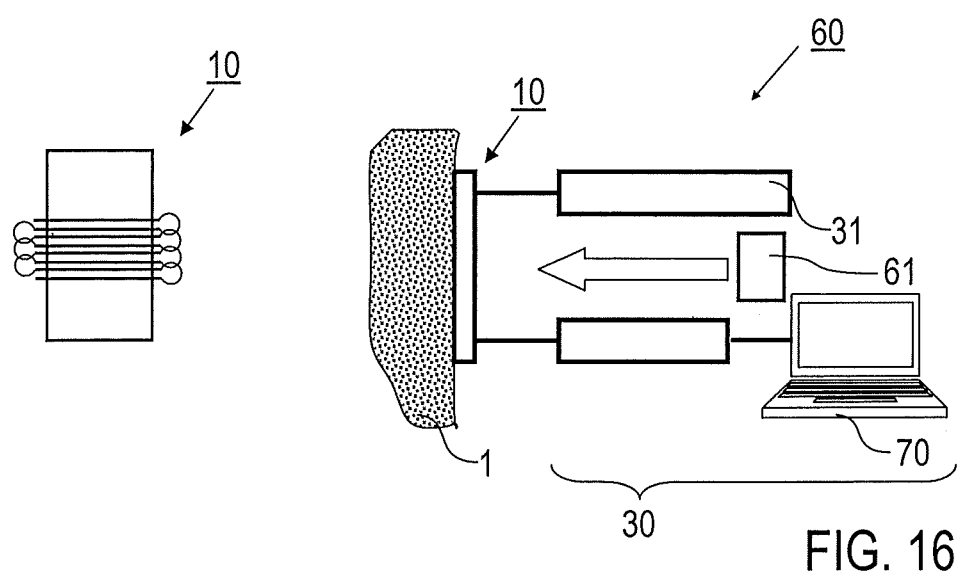

Further examples of the imaging apparatus 60 including the ultrasound detector 10, an interrogation device 30 with an interrogation light source 31, an excitation device 61, and a processor unit 70 are schematically illustrated in FIGS. 15 and 16. The processor unit 70 is arranged to reconstruct images based on the detected ultrasound signals. These examples are particularly adapted for non-invasive imaging of an extended object 1 using multiplexed π-phase shifted FBG sensors.

The FBG-based ultrasound detector 10 described above is used in the thermoacoustic imaging apparatus 60. The scheme may use a single Bragg grating, or alternatively multiplexed Bragg gratings for high throughput. The excitation device 61 emits electromagnetic pulses in either the optical regime or radio-frequency regime. Both the excitation and detection are performed outside the imaged object 1, e.g., biological tissue. To perform the imaging, the space between the ultrasound detector 10 and the imaged object 1 should have acoustic properties similar to biological tissue. Specifically, water or ultrasound gel may be used. Since the gratings in the ultrasound detector 10 are transparent and insensitive to electromagnetic radiation, the exciting electromagnetic fields may pass through the ultrasound detector 10. This allows for many degrees of freedom in the design compared to piezo-electric based schemes, in which, because the detectors interact with the exciting photons, the detectors must be positioned such that they do not come between the exciting source and imaged object.

Excitation-detection geometries reported in the previous art (e.g., Buehler A et al. "Video rate optoacoustic tomography of mouse kidney perfusion," OPTICS LETTERS; 35(14); 2475-7 (2010), Ma R et al. "Multispectral optoacoustic tomography (MSOT) scanner for whole-body small animal imaging," OPTICS EXPRESS 17(22); 21414-21426 (2009)) can be implemented with our imaging apparatus replacing the original one. In addition, new thermoacoustic imaging schemes can be specifically designed for the proposed FBG-based detection scheme.

FIGS. 15 and 16 show proposed detection geometries for cylindrical and planar detection, respectively. Both geometries can be used with just a single FBG written in the optical fiber of the ultrasound detector 10, although the envisioned application involves maximizing the number of gratings in the fiber. In both geometries, the FBG's may be positioned along the fiber 11 in various ways depending on the application. Two extreme options are having the FBG's written as close as possible to each other, maximizing the number of gratings per length, or as far away from each other over the given length of the detection, maximizing the detection length. Other geometries can be obtained by arranging the optical fiber along a predetermined reference surface with a plane or curved extension in space.

In the cylindrical geometry (FIG. 15), the optical fiber 11 of the ultrasound detector 10 is wrapped around the imaged object 1, or around a holder 4 in which it lies. In the case in which there are not sufficient gratings in the fiber for the desired application, the fiber 11 and/or holder may be translated and/or rotated to achieve additional detection points. Alternatively, the fiber 11 may be pulled along a rail to achieve that effect. In the planar geometry (FIG. 16), the fiber 11 is twisted to fit the rectangular detection area. Within the detection area, a set of straight parallel fiber sections is achieved, whereas at the edges the fiber is twisted.

The fiber 11 may be laid directly on the imaged object 1, or on a membrane or a rigid plate which is in contact with the imaged (directly or through an appropriate acoustic medium). In the case in which there are not sufficient gratings in the fiber for the desired application, the fiber and its backing may be translated horizontally and/or vertically and/or rotated to achieve additional detection points. Alternatively, the fiber may be pulled along a rail to achieve that effect. Addition in-between geometries, in which the detection area is curved but open follow directly from the proposed geometries.

Preferably, the photon flux density on the face of the imaged object 1 is as uniform as possible. This can be readily achieved because of the weak interaction between the detector and exciting electromagnetic fields. Subsequently, the exciting photons can pass through the ultrasound detector 10 without being affected or affecting the detection. In the cylindrical geometry, the exciting fields are either administrated from one or several sides of the imaged object, whereas in the planar geometry, the administration is performed from behind the detectors.

A volumetric image can be reconstructed from the measured acoustic signals using methods described in the previous arts. Specifically, back-projection algorithms or model-based algorithms may be used. When the wavelength of the exciting photons is in the optical domain, multiple wavelengths can be used to obtain a multi-spectral image that can be used to detect specific biomarkers. The effect of light attenuation can be corrected for by using light-propagation models or methods which exploit the spatial properties of the flight fluence function.

The features of our methods and devices in the above description, the drawings and the appended claims can be of significance both individually as well in combination.

The invention claimed is:

1. An ultrasound detector configured for ultrasound detection with medical applications comprising:
    an optical waveguide, and
    at least one Bragg grating, created with a predetermined refractive index modulation amplitude in the optical waveguide, wherein the at least one Bragg grating includes a localized defect in periodicity that causes a localized-light resonance portion configured to be formed around the defect, and said localized-light resonance portion has spectral properties configured to be modulated in response to an ultrasound oscillation, wherein the optical waveguide is a non-amplifying optical medium,
    the refractive index modulation amplitude is configured to be selected such that the localized-light resonance portion is configured to be concentrated at the defect in periodicity and the ultrasound oscillation is configured to be sensed by the at least one Bragg grating with an acoustic sensitivity most of which being obtained over the localized-light resonance portion, and
    wherein the optical waveguide is arranged along a reference surface with a plane or curved extension in space.

2. The ultrasound detector according to claim 1, wherein the optical waveguide comprises an optical fiber and the at least one Bragg grating comprises π-phase shifted Fiber Bragg Grating (FBG), or
    the optical waveguide comprises a planar waveguide and the at least one Bragg grating comprises π-phase shifted Waveguide Bragg Grating (WBG).

3. The ultrasound detector according to claim 1,
    wherein at least one of the optical waveguide is a single mode optical fiber,
    the optical waveguide is a polarization maintaining optical fiber,
    the optical waveguide comprises an optical fiber and the at least one π-phase shifted FBG is created at a free end of the optical fiber,
    the optical waveguide includes one single FBG or WBG, and
    the optical waveguide is transparent and insensitive to electromagnetic radiation at least at a position of the at least one π-phase shifted FBG or WBG, is satisfied.

4. The ultrasound detector according to claim 1, wherein the optical waveguide comprises an optical fiber and a free end of the optical fiber has at least one of
    a slanted tip laterally reflecting illumination light guided in the optical fiber to a surrounding region of the optical fiber, and
    a focusing element focusing illumination light guided in the optical fiber.

5. The ultrasound detector according to claim 4, wherein the slanted tip has a slanting angle selected such that the illumination light is reflected to a surrounding region located adjacent to a longitudinal position of the localized-light resonance portion of the at least one π-phase shifted FBG.

6. The ultrasound detector according to claim 1, wherein the optical waveguide includes multiple π-phase shifted FBG's or WBG's created in series in the optical waveguide.

7. The ultrasound detector according to claim 6, wherein at least one of
    the π-phase shifted FBG's or WBG's are created in the optical waveguide such that the a spectral defect resonance of each defect resonance portion is located outside a spectral bandgap of all other π-phase shifted FBG's or WBG's, and
    the π-phase shifted FBG's or WBG's are created in the optical waveguide with different periods so that the spectral properties of each defect resonance portion are modulated outside a spectral bandgap of all other π-phase shifted FBG's or WBG's, is satisfied.

8. An ultrasound detecting device, comprising:
    the ultrasound detector according to claim 1, and
    an interrogation device coupled with the at least one ultrasound detector and including an interrogation light source.

9. The ultrasound detecting device according to claim 8, configured for optoacoustic or thermoacoustic imaging an object under investigation.

10. The ultrasound detecting device according to claim 8, wherein the interrogation light source includes a pulsed laser source.

11. The ultrasound detecting device according to claim 10, wherein at least one of the pulsed laser source creates light pulses having a duration below 1 ns, in particular below 50 ps, and
    the pulsed laser source has an output such that no or negligible power is created outside the duration of the light pulses, is satisfied.

12. The ultrasound detecting device according to claim 11, wherein the pulsed laser source is coupled with an optically dispersive element extending duration of the light pulses.

13. The ultrasound detecting device according to claim 8, wherein the interrogation device includes at least one wavelength meter configured to detect a modulation of spectral properties in response to an ultrasound oscillation.

14. The ultrasound detecting device according to claim 13, wherein the wavelength meter is configured to detect a modulation of spectral properties in the reflection mode, the ultrasound detecting device further comprising a spectral inversion device configured for interfering detecting light reflected by the at least one π-phase shifted FBG or WBG with a reference beam such that destructive interference is obtained in all wavelengths but those of the spectral properties which are modulated in response to an ultrasound oscillation.

15. The ultrasound detecting device according to claim 14 wherein
   the spectral inversion device comprises an optical splitter and a Michelson interferometer with two interferometer arms, wherein
   the optical splitter is arranged to direct light from the interrogation light source into the interferometer arms,
   the π-phase shifted FBG or WBG is arranged in one of the interferometer arms, and
   a reflector is arranged in the other interferometer arm.

16. The ultrasound detecting device according to claim 8, wherein the optical waveguide includes multiple π-phase shifted FBG's or WBG's created in series in the optical waveguide, the ultrasound detecting device further comprising an optical wavelength demultiplexer device.

17. The ultrasound detecting device according to claim 16, wherein multiple wavelength meters are arranged at an output of the optical wavelength demultiplexer device to spectrally selectively detect a modulation of spectral properties of the detecting light transmitted by the multiple π-phase shifted FBG's or WBG's in response to an ultrasound oscillation.

18. The ultrasound detecting device according to claim 8, wherein
   a Mach-Zehnder modulator is arranged between the π-phase shifted FBG or WBG, and the optical wavelength demultiplexer device, or
   a Mach-Zehnder modulator is arranged between the interrogation light source and the π-phase shifted FBG or WGB, wherein detecting light input into or transmitted by the multiple π-phase shifted FBG's or WBG's is intensity modulated using the Mach-Zehnder modulator, and
   light sensitive elements are arranged at an output of the optical wavelength demultiplexer device, whose output is filtered around a modulation frequency of the Mach-Zehnder modulator.

19. The ultrasound detecting device according to claim 8, wherein the interrogation device includes one single interrogation light source.

20. Imaging apparatus comprising:
   an excitation device configured to generate ultrasound in an object by an electromagnetic field input, and
   the ultrasound detecting device according to claim 8.

21. The imaging apparatus according to claim 20, configured for optoacoustic or thermoacoustic imaging an object under investigation.

22. The imaging apparatus according to claim 20, wherein the excitation device includes an illumination waveguide configured to illuminate the object under investigation.

23. The imaging apparatus according to claim 22, further comprising a tube-shaped enclosure accommodating the illumination waveguide and the optical fiber of the ultrasound detector.

24. The imaging apparatus according to claim 23, wherein the illumination waveguide and the optical fiber are positioned such that an offset between the localized defect resonance portion in the at least one π-phase shifted FBG and a tip of the illumination waveguide is smaller than 1 cm.

25. The imaging apparatus according to claim 22, wherein the illumination waveguide is included in the optical fiber of the ultrasound detector.

26. The imaging apparatus according to claim 21, further comprising a drive mechanism configured for at least one of rotating and translating of at least one of the illumination waveguide and the ultrasound detector relative to the object under investigation.

27. The imaging apparatus according to claim 21, configured as an intravascular optoacoustic imaging apparatus.

28. A method of detecting ultrasound oscillations emanating an object under investigation comprising:
   creating the ultrasound oscillations in the object under investigation,
   subjecting at least one ultrasound detector comprising:
      an optical waveguide, and
      at least one Bragg grating, created with a predetermined refractive index modulation amplitude in the optical waveguide, wherein the at least one Bragg grating includes a localized defect in periodicity so that a localized-light resonance portion is configured to be formed around the defect, and said localized-light resonance portion has spectral properties configured to be modulated in response to an ultrasound oscillation, wherein
      the optical waveguide is a non-amplifying optical medium, and
      the refractive index modulation amplitude is configured to be selected such that the localized-light resonance portion is configured to be concentrated at the defect in periodicity and the ultrasound oscillation is configured to be sensed by the at least one Bragg grating with an acoustic sensitivity most of which being obtained over the localized-light resonance portion, to the ultrasound oscillations, and
   interrogating the at least one Bragg grating included in the optical waveguide using the ultrasound detecting device according to claim 8.

29. The method according to claim 28, wherein the ultrasound oscillations are created with an excitation device configured to generate ultrasound in the object by an electromagnetic field input in an optical band or an RF band, said excitation device being arranged with a distance from the object or within the object.

30. The method according to claim 28, further comprising the step of arranging the ultrasound detector in a vascular portion of a biological organism.

31. The method according to claim 30, further comprising the step of moving the ultrasound detector in the vascular portion of the biological organism.

32. The method according to claim 31, further comprising the step of arranging the at least one ultrasound detector on a surface of an object under investigation.

33. The method according to claim 29, further comprising the step of arranging the at least one ultrasound detector at a distance from the surface of the object under investigation, where a medium between the object and the at least one ultrasound detector is acoustically matched to the imaged object.

34. An ultrasound detector configured for ultrasound detection with medical applications comprising:
- an optical waveguide, and
- at least one Bragg grating, created with a predetermined refractive index modulation amplitude in the optical waveguide, wherein the at least one Bragg grating includes a localized defect in periodicity that causes a localized-light resonance portion configured to be formed around the defect, and said localized-light resonance portion has spectral properties configured to be modulated in response to an ultrasound oscillation, wherein the optical waveguide is a non-amplifying optical medium,
- the refractive index modulation amplitude is configured to be selected such that the localized-light resonance portion is configured to be concentrated at the defect in periodicity and the ultrasound oscillation is configured to be sensed by the at least one Bragg grating with an acoustic sensitivity most of which being obtained over the localized-light resonance portion, and wherein at least one of
- the at least one Bragg grating comprises a $\pi$-phase shifted Fiber Bragg Grating (FBG) or a $\pi$-phase shifted Waveguide Bragg Grating (WBG) created with a core refractive index modulation of at least $1\times10^{-4}$,
- the at least one Bragg grating comprises a $\pi$-phase shifted FBG created with a grating coupling coefficient above $\kappa=0.5$ mm$^{-1}$,
- the longitudinal extension of the localized-light resonance portion is below 1.5 mm,
- the at least one Bragg grating comprises a $\pi$-phase shifted grating which has a length below 1 cm, and
- the spectral width of the grating band gap in transmission is above 0.4 nm, is satisfied.

* * * * *

UNITED STATES PATENT AND TRADEMARK OFFICE
CERTIFICATE OF CORRECTION

PATENT NO. : 9,949,717 B2
APPLICATION NO. : 13/982019
DATED : April 24, 2018
INVENTOR(S) : Amir Rozental et al.

It is certified that error appears in the above-identified patent and that said Letters Patent is hereby corrected as shown below:

Column 6, Line 36 reads, ". . . value corresponds to a an" which should read ". . . value corresponds to an"

Column 7, Line 6 reads, ". . . detector includes may include . . ." which should read ". . . detector may include . . ."

Column 11, Lines 54-55 read, ". . . the apparatus is includes . . ." which should read ". . . the apparatus includes . . ."

Column 16, Lines 43-44 read, ". . . demultiplexer devices 50 are described . . ." which should read ". . . demultiplexer devices 50 is described . . ."

Column 17, Line 27 reads, ". . . ultrasound regime lead . . ." which should read ". . . ultrasound regime leads . . ."

Column 21, Line 40 reads, ". . . individually as well in combination . . ." which should read ". . . individually as well as in combination . . ."

Column 22, Line 37 reads, ". . . that the a spectral . . ." which should read ". . . that a spectral . . ."

Signed and Sealed this
Tenth Day of July, 2018

Andrei Iancu
*Director of the United States Patent and Trademark Office*